(12) United States Patent
Klöti et al.

(10) Patent No.: US 6,353,155 B1
(45) Date of Patent: Mar. 5, 2002

(54) METHOD FOR TRANSFORMING PLANTS

(75) Inventors: Andreas S. Klöti, Durham; Rao Mulpuri, Morrisville, both of NC (US)

(73) Assignee: Paradigm Genetics, Inc., Research Triangle Park, NC (US)

( * ) Notice: Subject to any disclaimer, the term of this patent is extended or adjusted under 35 U.S.C. 154(b) by 0 days.

(21) Appl. No.: 09/607,306

(22) Filed: Jun. 30, 2000

(51) Int. Cl.$^7$ .............................. A01H 1/00; A01H 5/00; C12N 5/10; C12N 15/84
(52) U.S. Cl. ....................... 800/294; 435/419; 435/469; 800/298
(58) Field of Search ................................ 435/469, 410, 435/420, 419; 800/294, 298

(56) References Cited

PUBLICATIONS

Clough et al, "Flip dip: a simplified method for Agrobacterium–mediated transformation of Arabidopsis thaliana", 1998, The Plant Journal, vol. 16(6), pp. 735–743.*

Bechtold et al., In Planta Agrobacterium–Mediated Transformation of Adult Arabidopsis thaliana Plants by Vacuum Infiltration, Methods in Molecular Biology, 82:259–266 (1998).

Ye et al., Arabidopsis ovule is the target for Agrobacterium in planta vacuum infiltration transformation, The Plant Journal, 19(3):249–257 (Aug. 1999).

* cited by examiner

*Primary Examiner*—Elizabeth F. McElwain
*Assistant Examiner*—Cynthia Collins
(74) *Attorney, Agent, or Firm*—Joseph T. Majka; Henry P. Nowak

(57) ABSTRACT

A method for preparing transgenic plants and seeds is claimed. The method is particularly useful for high-throughput transformation of plants, such as *Arabidopsis thaliana*, using many different types of DNA sequences of interest.

25 Claims, No Drawings

METHOD FOR TRANSFORMING PLANTS

FIELD OF THE INVENTION

The present invention relates to improved, simplified method for transforming plants using a bacteria known as Agrobacterium.

BACKGROUND OF THE INVENTION

Recent advances in genetic engineering have provided plant breeders and geneticists with the tools to insert or transform new genetic material, usually in the form of DNA (deoxyribonucleic acid) fragments, into a plant in order to produce new kinds of plants known as transgenic plants. Such transgenic plants or crops can have unique characteristics or traits, including resistance to plant diseases, resistance to herbicides, resistance to insects, enhanced stability or shelf-life of the ultimate consumer product obtained from the plant and/or improvements in the nutritional value in the edible portions of the plant. In agriculture, a bacterium known as *Agrobacterium tumefaciens* was discovered to have the property of being able to naturally infect a host plant, and insert and integrate a portion of its DNA into the host plant's DNA. Since then, this DNA transfer mechanism has been harnessed a way to produce genetically engineered transgenic plants.

Recent scientific publications such as Bechtold et al., Methods Mol. Biol. 82:259–266 (1998); Clough et al., Plant J, 16(6):735–743 (1998); and Ye et al., Plant J., 19(3): 249–257 (August 1999) teach lengthy methods for in planta transformation of *Agrobacterium thaliana*. In these methods, a suspension of Agrobacterium is initially grown. Then the suspension is transferred to a centrifugation bottle and the bacterial cells are pelleted by spinning the centrifugation bottles on a centrifugation machine. The pelleted Agrobacteria are resuspended in a media for transforming a plant. Finally, the plants are contacted with the resuspended media for the transformation process. Although effective, such methods have the disadvantage of being time consuming and requiring expensive centrifuges to prepare the Agrobacterium. Such disadvantages are become multiplied for applications of high-throughput transformation of plants using many different types of genes or DNA. Thus, in order to prepare transgenic plants or seeds, a new approach was sought to transform plants with Agrobacterium that would be more efficient and less costly than previous methods.

SUMMARY OF THE INVENTION

In one embodiment, the present invention is directed towards a method for preparing a transgenic plant or seed comprising:
  a) growing a suspension of Agrobacterium until the optical density of the suspension is about 2 to about 2.4 at a wavelength of 600 nanometers, wherein said Agrobacterium contains at least one plasmid having a DNA sequence of interest flanked by T-DNA borders;
  b) diluting said suspension with an aqueous medium so that the optical density of the suspension is reduced to about 0.6 to about 1.5; and
  c) treating the flower of said plant with said diluted suspension so that the Agrobacterium in said diluted suspension can transform said plant with the DNA-sequence of interest;
  d) optionally; cultivating said treated plant to produce seed; and
  e) optionally; growing plants from said seed and selecting for transgenic plants having said DNA sequence of interest.

In a second embodiment, the present invention is directed toward a method for preparing a transgenic plant or seed comprising:
  a) growing a suspension of Agrobacterium until growth of Agrobacterium in the suspension is substantially completed, wherein said Agrobacterium contains at least one plasmid having a DNA sequence of interest flanked by T-DNA borders;
  b) diluting said suspension with an aqueous medium to reduce the concentration of Agrobacterium and any other components in the growth medium and allow the Agrobacterium to infect the plant without harming it;
  c) treating the flower of said plant with said diluted suspension so that the Agrobacterium in said diluted suspension can transform said plant with the DNA-sequence of interest;
  d) optionally, cultivating said treated plant to produce seed; and
  e) optionally, growing plants from said seed and selecting for transgenic plants having said DNA sequence of interest.

In a third embodiment, the present invention is directed toward a method for preparing a transgenic plant or seed comprising:
  a) growing a suspension of Agrobacterium until growth of Agrobacterium in the suspension is substantially completed, wherein said Agrobacterium contains at least one plasmid having a DNA sequence of interest flanked by T-DNA borders;
  b) diluting said suspension with about 2 to about 10 volumes aqueous medium per volume of suspension;
  c) treating the flower of said plant with said diluted suspension so that the Agrobacterium in said diluted suspension can transform said plant with the DNA-sequence of interest;
  d) optionally, cultivating said treated plant to produce seed; and
  e) optionally, growing plants from said seed and selecting for transgenic plants having said DNA sequence of interest.

Preferably, the Agrobacterium is *Agrobacterium tumefaciens*. Also preferred is that the plant is Arabidopsis. Also preferred is that the aqueous medium contains a surfactant, sugar or both.

The present invention has the advantage of providing a method for transforming plants that requires significantly less time and personnel to perform compared with other known methods.

Another advantage of the present invention is that it eliminates the need to use expensive centrifuges to prepare the Agrobacterium cultures.

Still yet another advantage is that it provides a method for high-throughput transformation of plants, such as *Arabidopsis thaliana*, using many different types of DNA sequences.

DETAILED DESCRIPTION OF INVENTION

Unless indicated otherwise, percentage (%) measurements are on a weight/weight (wt/wt) basis.

The terms "DNA of interest," "DNA sequence," "T-DNA," "recombinant DNA," "recombinant DNA sequence" and "recombinant polynucleotide" can be used interchangeably to refer to recombinant DNA that is transferred from Agrobacterium to the plant or plant cell via the transformation process.

"Recombinant DNA" refers to DNA that has been altered, rearranged, isolated or modified by genetic engineering.

Examples include any cloned DNA, and polynucleotides that are linked or joined to heterologous sequences. Two polynucleotide sequences are heterologous if they are not naturally found joined together. The term "recombinant" does not refer to alterations to polynucleotides that result from naturally occurring events, such as spontaneous mutations.

"T-DNA" refers to the DNA sequence, a copy of which gets transferred from Agrobacterium to the plant cell.

"T-DNA borders" borders refers to the DNA sequences that flank the T-DNA.

The term "transforming" or "transformation" refers to the process of introducing DNA into a recipient plant cell and its subsequent integration into the plant cell's chromosomal DNA. The DNA comes from a large plasmid in the Agrobacterium known as the Ti (Tumour induction) plasmid. Naturally, such a Ti-plamid comprises several vir (virulence) genes, whose products are directly involved in T-DNA processing and transfer. Located within the natural T-DNA are genes for plant growth regulators and amino acid derivatives, which are for the sole benefit of the Agrobacterium, but are not necessary for the transfer of the T-DNA and its integration into the plant genome. Such natural Ti-plasmids are therefore very large. To make it useful for the purpose of plant transformations, two changes have been made to these Ti-plasmids:
1. All the genes within the T-DNA have been removed and can now be replaced with any DNA sequence that one wants to transfer to the plant cell.
2. The T-DNA itself is removed from the Ti-plamid and is placed on a novel plasmid called the binary vector. Together with the Ti-plasmid, this binary vector co-exists and and replicates within Agrobacterium. Since the binary vector is relatively small it is relatively easy to work with. A copy of a short region of DNA (called T-DNA) in the binary vector is transferred to the plant cell, where it becomes stably integrated into the plant genome, i.e. the plant cell's chromosomal DNA. The construction of binary vectors containing T-DNAs capable of being inserted into a plant genome via Agrobacterium mediated delivery is known to those skilled in the art. In addition to the DNA sequence of interest, a selectable marker gene can be placed within the T-DNA borders in order to allow selection for plants transformed with the DNA sequence of interest. Such selectable marker genes include aph4, for hygromycin resistance, npt2, for kanamycin resistance, bar for Basta resistance, cp4 for glyphosate resistance.

The term "plasmid" refers to a small, independently replicating piece of DNA (i.e. exists inside a bacterial cell separate from the bacteria's main DNA).

"Transgenic" refers to a plant, plant cell, plant tissue, plant part or seed that contains all or part of at least one recombinant DNA or polynucleotide sequence. In many cases, all or part of the recombinant polynucleotide is stably integrated into a chromosome or stable extra-chromosomal element, so that it is passed on to successive generations. For purposes of this invention, a plant is considered transgenic if it contains recombinant DNA in only some, but not all tissues, i.e. only in flowers or reproductive tissues.

Plants suitable for transformation can include, dicots or dicotyledonous plants (two seed leaves or cotyledons) having at least one flowering part or bolt that can be infected or transformed, including Arabidopsis, tomatoes, soybeans, cotton, oilseed rape, flax, sugar beet, sunflower, potato, tobacco, lettuce, peas, beans, alfalfa and the like. Monocots or monocotyledonous plants (one cotyledon) such as rice, maize, wheat, sorghum and the like may also be transformed, but with a lesser degree of success as the dicots. For transformation, the plant is grown to its adult stage, i.e. when it starts flowering. The combination of flowers on an Arabidopsis stem is referred to as the "flower bolt" or "bolt." In certain species such as Arabidopsis, the primary flower bolt or bolt is sometimes removed to encourage growth of multiple secondary flower bolts or bolts.

The term "flower" refers to the reproductive organs of a plant or to tissues that can later develop and/or differentiate into the reproductive organs or parts thereof. When flowers or a bolt with one or more flowers is present on the plant, the plant is ready for treatment with Agrobacterium.

The term "Agrobacterium" refers to a gram-negative, rod-shaped, flagellated bacterium responsible for crown gall tumour in plants, including *Agrobacterium tumefaciens* or *Agrobacterium rhizogenes*. Suitable strains of *Agrobacterium tumefaciens* includes strains GV3101 and LB4404.

The term "suspension" refers to a system in which very small bacterial particles are more or less uniformly dispersed in a liquid water or aqueous medium. The optical density of the initial suspension and/or the diluted suspension can be measured using a spectrophotometer at a wavelength of 600 nanometers (nm).

The initial suspension can be prepared by growing Agrobacterium in an aqueous medium containing ingredients for growth of the bacteria. One such growth media is known as Lennox L broth base bacterial growth medium (LB) which contains 1% w/v Peptone 140 (pancreatic digest of casein), 0.5% yeast extract (water soluble portion of autolyzed yeast with intact B-complex vitamins), 0.5% wt/v sodium chloride and a suitable antibiotic for maintenance of the binary vector in the Agrobacterium cell. Suitable antibiotics can include kanamycin, streptomycin, tetracycline, hygromycin and the like. Other growth media are described in Murashige T. and Skoog F., A revised medium for rapid growth and bioassays with tobacco tissue cultures. Physiol Plant 15: 473–497 (1962).

The initial suspension of Agrobacterium is cultivated or grown until growth of Agrobacterium in the suspension is substantially completed, i.e. the density of bacteria in the suspension has reached near-maximum levels over time. Typically, the growth of Agrobacterium in the suspension is substantially completed after 16 to 24 hours, although longer or shorter times may be used. The optical density of the initial suspension can range from about 1.2 to about 2.4 or greater.

After the initial suspension of Agrobacterium is grown or formed, it is diluted with an aqueous medium to reduce the Agrobacterium and any other components in the growth medium (i.e. antibiotics) to a concentration that will allow the Agrobacterium to infect the plant without harming it. Typically, the initial suspension can be diluted by mixing from about 2 to about 10 volumes of aqueous medium per one volume of initial suspension, preferably from about 3 to about 5 volumes of aqueous medium. The optical density of the diluted suspension is less than 2, preferably from about 0.6 to about 1.5, more preferably from about 0.8 to about 1.0.

The aqueous medium used to dilute the initial suspension may optionally contain adjuvants or additives which can promote or enhance transformation by Agrobacterium, such as sugars and surfactants. Suitable sugars can include sucrose, fructose, glucose, galactose and the like. When sugars are used, the concentration of sugar in the aqueous medium can range from about 2 to about 10% by weight, preferably about 5% by weight.

The term "surfactant" or "surface-active agent" refers to any compound that can reduce surface tension when dissolved in water or water solutions or that can reduce interfacial tension between a liquid (water) and a solid (bacteria). Generally, the surfactant should not be harmful to the plant. Suitable surfactants that can be used in the aqueous medium can include Triton™ brand of surfactants, the Tween™ m brand of surfactants and the Silwet™ brand of surfactants. The Triton™ brand of surfactants includes specialty surfactants that are alcohols and ethoxylates, alkoxylates, sulfates, sulfonates, sulfonosuccinates or phosphate esters. One preferred surfactant is Triton™ X-100 (t-Octylphenoxypolyethoxyethanol) a widely used nonionic surfactant. Another preferred surfactant is Silwet-L77® (polyalkyleneoxide modified heptamethyltrisiloxane). The concentration of surfactant in the aqueous medium can range from about 0.001 to about 0.5% by weight, preferably from about 0.01 to about 0.05%.

To transform or treat the plant, the flower or bolt is contacted with the diluted suspension of Agrobacterium. For example, the flower can be dipped into diluted suspension containing the Agrobacterium for about 10 seconds to one minute or more. Alternatively, the diluted suspension of Agrobacterium can be sprayed or painted onto the flower portions of the plant.

After the plants have been treated with the diluted suspension of Agrobacterium, they are typically placed for one day into a dark room or chamber having a high relative humidity to encourage the Agrobacterium to infect or transform the plant. The temperature is maintained from about 20 to about 30 degrees Celcius, preferably from about 22 to about 25 degrees Celcius (room temperature).

Optionally, and preferably, the treated plants are grown or cultivated under normal growth conditions to produce seed or to seed maturity.

Optionally, and preferably, seed that is collected or harvested may be grown into plants. Plants that have been transformed, i.e. that are transgenic due to the insertion of recombinant DNA or DNA of interest into their genome, may be selected by treating the plants with an antibiotic or herbicide and selecting those with antibiotic or herbicide resistance, an indicator of transformation.

The present method can be used without a vacuum or with a vacuum as described in Bechtold et al., Methods Mol. Biol. 82:259–266 (1998).

The following examples are provided to show various embodiments in which the present invention can be carried out, but is not intended to limit the scope of the claimed invention.

EXAMPLE

Transformation of *Arabidopsis thalina*, ecotype Columbia

A culture of Agrobaterium is grown in 50 milliliters (mL) of LB medium in sterile, disposable 330 mL containers that are suitable for dipping *Arabidopsis thaliana* plants in these containers. When the Agrobacteria have grown to a high density (optical density of 2.0 or more at 600 nm), the Agrobacteria suspension is diluted with 4 volumes of a 6% sucrose solution containing Silwet L-77. The diluted suspension of Agrobacteria has an optical density of about 0.8 to about 1.0 and the Silwet L-77 concentration in the diluted suspension is about 0.03%. Subsequently, the flower bolts of *Arabidopsis thaliana* plants are directly dipped into the diluted suspension of Agrobacterium for about 10 seconds. After dipping, the plants are kept upright in the dark overnight and are then further cultured in the growth room until the seeds of the plants are harvested 28 days after dipping. The harvested seed are germinated and grown into seedlings. Selection for transgenic seedlings is applied, using either herbicides or antibiotics, depending upon the selectable marker gene. Seedlings surviving the selection process are indicative of transgenic plants derived from harvested transgenic seed. Most of the seed produced by such transgenic plants will also be transgenic. The number of transformed plants obtained using this simplified method is at least as high as the number of transformed plants obtained using methods including pelleting via centrifugation with subsequent resuspension.

What is claimed is:

1. A method for preparing a transgenic plant or seed comprising:
    a) growing a suspension of Agrobacterium cells until the optical density of the suspension is about 2 to about 2.4 at a wavelength of 600 nanometers, wherein said Agrobacterium cells contain at least one plasmid having a DNA sequence of interest flanked by T-DNA borders;
    b) diluting said Agrobacterium cells of said suspension with an aqueous medium so that the optical density of the suspension is reduced to about 0.6 to about 1.5, wherein said diluting is not followed by pelleting via centrifugation with subsequent resuspension; and
    c) treating the flower of said plant with said diluted suspension so that the Agrobacterium cells in said diluted suspension can transform said plant with the DNA-sequence of interest;
    d) optionally, cultivating said treated plant to produce seed; and
    e) optionally, growing plants from said seed and selecting for transgenic plants having said DNA sequence of interest.

2. The method of claim 1 wherein said Agrobacterium is *Agrobacterium tumefaciens*.

3. The method of claim 1 wherein said plant is Arabidopsis.

4. The method of claim 1 wherein said aqueous medium contains a surfactant.

5. The method of claim 1 wherein said aqueous medium contains sugar.

6. The method of claim 1 wherein said aqueous medium contains surfactant and sugar.

7. The method of claim 1 wherein step b), the optical density of the suspension is reduced to about 0.8 to about 1.0 at a wavelength of 600 nanometers.

8. The method of claims 1, further comprising cultivating said treated plant to produce seed.

9. The method of claim 8 further comprising growing plants from said seed and selecting for transgenic plants having said DNA sequence of interest.

10. A method for preparing a transgenic plant or seed comprising:
    a) growing a suspension of Agrobacterium cells until growth of Agrobacterium cells in the suspension is substantially completed, wherein said Agrobacterium cells contain at least one plasmid having a DNA sequence of interest flanked by T-DNA borders;
    b) diluting said suspension with an aqueous medium to reduce the concentration of Agrobacterium cells and any other components in the growth medium and allow the Agrobacterium cells to infect the plant without harming it, wherein said diluting is not followed by pelleting via centrifugation with subsequent resuspension;
    c) treating the flower of said plant with said diluted suspension so that the Agrobacterium cells in said diluted suspension can transform said plant with the DNA-sequence of interest;

d) optionally, cultivating said treated plant to produce seed; and e) optionally, growing plants from said seed and selecting for transgenic plants having said DNA sequence of interest.

11. The method of claim 10 wherein said Agrobacterium is *Agrobacterium tumefaciens*.

12. The method of claim 10 wherein said plant is Arabidopsis.

13. The method of claim 10 wherein said aqueous medium contains a surfactant.

14. The method of claim 10 wherein said aqueous medium contains sugar.

15. The method of claim 10 further comprising cultivating said treated plant to produce seed.

16. The method of claim 15 further comprising growing plants from said seed and selecting for transgenic plants having said DNA sequence of interest.

17. A method for preparing a transgenic plant or seed comprising:

a) growing a suspension of Agrobacterium cells until growth of Agrobacterium cells in the suspension is substantially completed, wherein said Agrobacterium cells contains at least one plasmid having a DNA sequence of interest flanked by T-DNA borders;

b) diluting said Agrobacterium cells in said suspension with about 2 to about 10 volumes aqueous medium per volume of suspension, wherein said diluting is not followed by pelleting via centrifugation with subsequent resuspension;

c) treating the flower of said plant with said diluted suspension so that the Agrobacterium cells in said diluted suspension can transform said plant with the DNA-sequence of interest;

d) optionally, cultivating said treated plant to produce seed; and e) optionally, growing plants from said seed and selecting for transgenic plants having said DNA sequence of interest.

18. The method of claim 17 wherein said Agrobacterium is *Agrobacterium tumefaciens*.

19. The method of claim 17 wherein said plant is Arabidopsis.

20. The method of claim 17 wherein said aqueous medium contains a surfactant.

21. The method of claim 17 wherein said aqueous medium contains sugar.

22. The method of claim 17 wherein said aqueous medium contains surfactant and sugar.

23. The method of claim 17 wherein step b) said suspension is diluted with from about 3 to about 5 volumes of aqueous medium.

24. The method of claim 17 further comprising cultivating said treated plant to produce seed.

25. The method of claim 21 further comprising growing plants from said seed and selecting for transgenic plants having said DNA sequence of interest.

* * * * *